United States Patent [19]

Parkola

[11] Patent Number: 5,569,294
[45] Date of Patent: Oct. 29, 1996

[54] TWO PIECE BALLOON PROTECTOR

[75] Inventor: Walter R. Parkola, El Cajon, Calif.

[73] Assignee: Medtronic, Inc., Minneapolis, Minn.

[21] Appl. No.: 312,338

[22] Filed: Sep. 26, 1994

[51] Int. Cl.$^6$ .................................................. A61M 25/00
[52] U.S. Cl. ............................................ 606/194; 604/96
[58] Field of Search ..................... 604/96, 103; 606/194; 206/363, 364, 438, 446

[56] References Cited

U.S. PATENT DOCUMENTS

| | | |
|---|---|---|
| 4,573,981 | 3/1986 | McFarlane . |
| 4,710,181 | 12/1987 | Fuqua . |
| 4,738,666 | 4/1988 | Fuqua . |
| 5,015,231 | 5/1991 | Keith et al. . |
| 5,053,007 | 10/1991 | Euteneuer . |
| 5,066,298 | 11/1991 | Hess . |
| 5,137,512 | 8/1992 | Burns et al. . |
| 5,352,236 | 10/1994 | Jurg et al. ............................ 606/194 |
| 5,417,707 | 5/1995 | Parkola ................................ 606/194 |
| 5,425,710 | 6/1995 | Khair .................................... 604/96 |

Primary Examiner—Corrine M. McDermott
Attorney, Agent, or Firm—Michael R. Shevlin; Dianne M. F. Plunkett; Harold R. Patton

[57] ABSTRACT

The present invention is for a two piece balloon protector (5) which consists of an cylindrical tube (10) and an inner elastomeric member (15). The inner elastomeric member (15) has a outer diameter that is smaller than the inner diameter of cylindrical tube (10) and fits inside of the cylindrical tube (10). The proximal end of the inner elastomeric member (15) has a return flange (30) that fits around the proximal end of cylindrical tube (10). To install the balloon protector (5) over the dilatation catheter balloon (20), cylindrical tube (10) is held fixed while the inner elastomeric member (15) is pulled longitudinally at its distal end, thus stretching the material, decreasing the longitudinal cross-section and creating a larger inner diameter in inner elastomeric member (15). The balloon protector (5) is slid over the dilatation catheter balloon (20), the longitudinal force on the inner insert (15) is released causing the inner diameter of the inner elastomeric member (15) to decrease, compressing and containing the dilatation catheter balloon (20).

3 Claims, 1 Drawing Sheet

TWO PIECE BALLOON PROTECTOR

FIELD OF THE INVENTION

This invention relates to the field of angioplasty, and more particularly to a balloon protector of a dilatation balloon catheter.

BACKGROUND OF THE INVENTION

Dilatation balloon catheters are frequently used for the treatment of stenoses in the coronary arteries. This procedure, known as percutaneous transluminal coronary angioplasty (PCTA), was developed by Dr. Andreas Gruntzig. According to this procedure, blockage in a coronary artery can be reduced by positioning a balloon dilatation catheter across the blockage and inflating the balloon, which causes stretching of the artery and pressing of the lesion into the artery wall to re-establish acceptable blood flow through the artery.

To move through the artery, the deflated balloon diameter should be as small as possible. The core or inner tube diameter of the catheter should be minimized along with the balloon, which can be done by folding, wrapping or twisting the balloon to achieve the smallest profile possible or by reducing wall thicknesses, to the extent possible, of the balloon itself. This deflated diameter affects the ease and ability of the dilatation catheter to pass through a guide catheter and through the coronary arteries leading to the stenosis to be opened.

In order to keep the outer diameter of the balloon catheter in its deflated condition, it is common to use a balloon protector. A balloon protector protects the balloon and distal tip of the catheter from possible damage during storage and keeps the balloon tightly wrapped in its deflated condition to minimize the outer diameter of the balloon in its deflated state. During the sterilization process, the catheter, with the balloon protector in place, is exposed to an elevated temperature for a period of time which causes the balloon to be heat set in the folded or wrapped configuration in which it is held by the balloon protector. This heat setting of a balloon gives the balloon a memory so that when it is inflated and deflated during an angioplasty procedure, the deflation will cause the balloon to return to its tightly wrapped heat set shape. This heat set shape will give the balloon a low profile diameter which will help when moving the catheter to a new stenosis or removal of the catheter after the procedure has been performed.

Various types and configurations of balloon protectors have been shown in the prior art, for example, in U.S. Pat. Nos. 4,738,666 and 4,710,181 to Fuqua, in U.S. Pat. No. 5,053,007 to Euteneuer, U.S. Pat. No. 5,066,298 to Hess, U.S. Pat. No. 4,573,981 to McFarlane, U.S. Pat. No. 5,015,231 to Keith et at. and U.S. Pat. No. 5,137,512 to Burns et at.

The above-noted Fuqua '666 and '181 patents propose a catheter protector comprising a hollow cylindrical sheath. The Fuqua sheath covers the entire length of the catheter, and is removed by pulling it off of the proximal end of the catheter. Fuqua also proposes providing perforations in the sheath for facilitating its removal. The above-noted Euteneuer '007 patent proposes a compression protector employing an inner sleeve applied over a deflated balloon, an outer sleeve applied over the inner sleeve, and a compression housing for compressing the outer sleeve radially in on the inner sleeve, thus compressing the inner sleeve radially in on the balloon. The above-noted Hess '298 patent proposes protecting a catheter's balloon by wrapping the balloon with tape in an overlapping fashion. The above-noted McFarlane '981 patent proposes a substantially tapered cylindrical sheath which encloses a distal portion of the catheter assembly and is locked in place with two finger elements. The above noted Keith '231 patent proposes a multipart balloon protector consisting of an inner sleeve, with an elongated expansion slit to facilitate installation over the balloon, and a second outer sleeve compressing the inner sleeve. The above noted Burns '512 patent proposes a multisegment balloon protector using two protectors that cover different areas of the balloon stating that by using several protectors, each of which fits over a part of the balloon, the force required to apply each protector individually is significantly less than a protector that extends over the entire length of the balloon.

There is a need for simple balloon protectors to protect the catheter distal sections, including catheter balloons because they have become smaller, thinner, and more fragile and it has become increasingly difficult to apply a balloon protector which does not damage the catheter or the balloon when installed.

SUMMARY OF THE INVENTION

Accordingly, the present invention is directed to an improved balloon protector for covering and protecting the balloon of a dilatation catheter. This invention is for a two piece balloon protector consisting of an outer cylindrical tube and an inner elastomeric member which, when pulled longitudinally, increases the inside diameter due to displacement of the material. When the inside diameter becomes larger, the protector may be slid over the dilatation catheter balloon fully and when the tension on the elastomer is relaxed it will decrease the inside diameter and compress the balloon. Having a balloon protector with a inner diameter that can be increased when installed over a balloon will lessen the risk of damage to the balloon and can be readily removed from the balloon prior to use, without the need for cutting or tearing the protector.

BRIEF DESCRIPTION OF THE DRAWINGS

The foregoing and other features of the present invention will be best appreciated with reference to the following detailed description of a specific embodiment of the invention, when read in conjunction with the accompanying drawings.

DETAILED DESCRIPTION OF THE PREFERRED EMBODIMENTS

Figure 1:
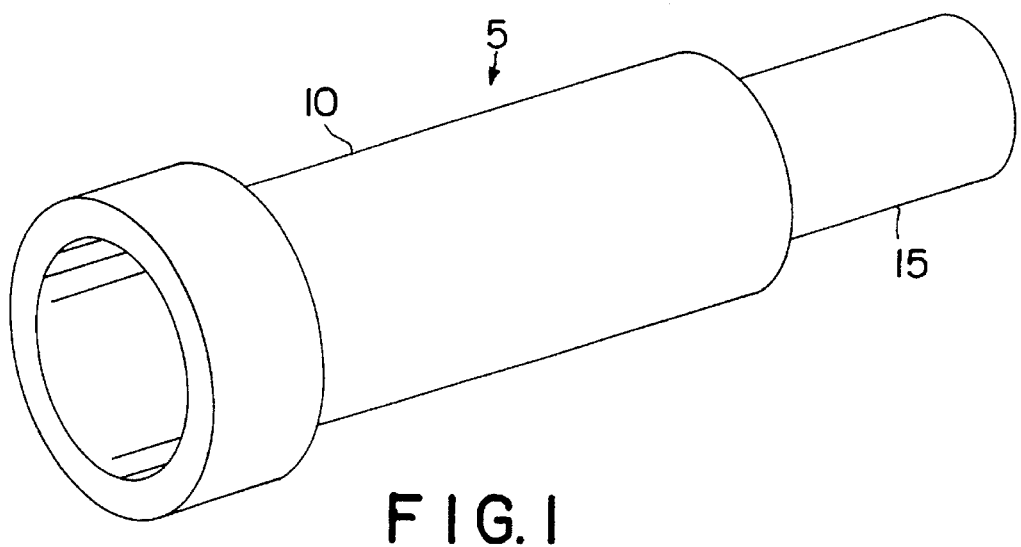
FIG. 1 is an enlarged perspective view of a balloon protector of the present invention.
Figure 2:
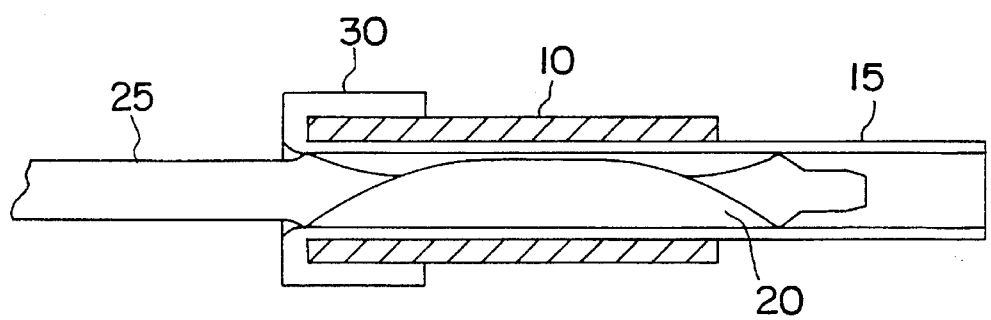
FIG. 2 is a longitudinal sectional view of the balloon protector of the present invention in its stretched position for assembly over a balloon.
Figure 3:
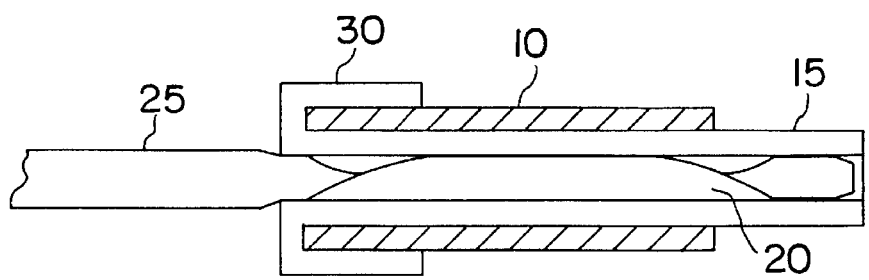
FIG. 3 is a longitudinal sectional view of the balloon protector of the present invention in its retracted position, as assembled on a balloon.

FIG. 1 shows a balloon protector 5 in accordance with an illustrative embodiment of the present invention. Balloon protector 5 consists of an cylindrical tube 10 and an inner elastomeric member 15. The cylindrical tube 10 can be made from any material (metal, plastic, etc.) that is rigid enough to perform its function. The inner elastomeric member 15 can be made from an elastomeric material, such as silicone, viton, etc., with material properties including cross-section reduction as tension force is longitudinally applied. The inner elastomeric member 15 has a outer diameter that is smaller than the inner diameter of cylindrical tube 10 and fits inside of the cylindrical tube 10. The proximal end of the inner elastomeric member 15 has a return flange 30 that fits around the proximal end of cylindrical tube 10 as shown in FIGS. 2 and 3. The return flange 30 is designed such that it will not detach from the cylindrical tube 10 when cylindrical tube 10 is held fixed while the inner elastomeric member 15 is pulled at its distal end.

FIG. 2 shows a sectional view of the installation of the balloon protector 5 over a dilatation catheter balloon 20. To install the balloon protector 5 over the dilatation catheter balloon 20, cylindrical tube 10 is held fixed while the inner elastomeric member 15 is pulled longitudinally at its distal end, thus stretching the material, decreasing the longitudinal cross-section and creating a larger inner diameter in inner elastomeric member 15. This inner diameter should be slightly larger than dilatation catheter balloon 20 in its deflated state. Once the inner diameter of the inner elastomeric member 15 is greater than the deflated outer diameter of the dilatation catheter balloon 20, the balloon protector 5 is slid over the dilatation catheter balloon 20 until the proximal end of the balloon protector 5 covers the proximal end of the dilatation catheter balloon 20. The longitudinal force on the inner insert 15 can now be released and doing so will cause the inner diameter of the inner elastomeric member 15 to decrease, compressing and containing the dilatation catheter balloon 20, as shown in FIG. 3.

Those of ordinary skill in the art will appreciate an advantageous feature of the present invention, namely, that in installing the balloon protector 5 over the dilatation catheter balloon 20, it is not necessary for protector 5 to be heated. Instead, protector 5 may be simply placed over the balloon 20 at room temperature and this will lower the risk of damage to the balloon.

A method of installing the balloon protector 5 around a dilatation catheter balloon 20 is accomplished by inserting the inner elastomeric member 15 through the cylindrical tube 10 until their proximal ends are engaged at the return flange 30. Securing the cylindrical tube 10 and pulling the distal end of the inner elastomeric member 15 longitudinally until it's inner diameter is greater the outer diameter of a dilatation catheter balloon 20. Sliding the balloon protector 5 over the dilatation catheter balloon 20 and releasing the inner elastomeric member 15, which reduces its diameter and protects the dilatation catheter balloon 20.

Although a particular embodiment of the invention has been described herein in some detail, this has been done for the purposes of illustration only and is not intended to be limiting with regard to the scope of the present invention as defined in the claims. It is contemplated that various substitutions, alterations, and/or modifications, including but not limited to those specifically discussed herein, may be made to the embodiment described herein without departing from the spirit and scope of the present invention.

| No. | Component |
| --- | --- |
| 5 | Balloon Protector |
| 10 | Cylindrical Tube |
| 15 | Inner Elastomeric Member |
| 20 | Dilatation Catheter Balloon |
| 25 | Catheter Shaft |
| 30 | Return Flange |

What is claimed is:

1. A method of installing a balloon protector around a dilatation catheter balloon comprising the steps of:

assembling a balloon protector by inserting an inner elastomeric member, having a proximal end and a distal end, through a cylindrical tube, having a proximal end and a distal end, until their proximal ends are engaged;

installing the balloon protector on a dilatation catheter balloon by securing the cylindrical tube;

pulling the distal end of the inner elastomeric member longitudinally until it's inner diameter is greater than the outer diameter of a dilatation catheter balloon;

sliding the balloon protector over the dilatation catheter balloon; and releasing the inner elastomeric member which reduces its diameter and protects the dilatation catheter balloon.

2. A method of installing a balloon protector around a dilatation catheter balloon comprising the steps of:

providing a balloon protector made by the steps comprising:

fabricating an inner elastomeric member, having a proximal end and a distal end;

fabricating, cylindrical tube, having a proximal end and a distal end;

inserting the inner elastic member through the cylindrical tube; and attaching the proximal end of the inner elastic member to the proximal end of the cylindrical tube;

providing a dilatation catheter balloon;

securing the cylindrical tube of the balloon protector and pulling the distal end of the inner elastomeric member longitudinally until it's inner diameter is greater than the outer diameter of a dilatation catheter balloon;

sliding the balloon protector over the dilatation catheter balloon; and releasing the inner elastomeric member which reduces its diameter and protects the dilatation catheter balloon.

3. A balloon protector for a dilatation catheter, comprising:

a cylindrical tube made of rigid material with a distal end and a proximal end;

an inner elastomeric member that is cylindrical with a distal end and a proximal end sized to slidably fit inside the cylindrical tube, the inner elastomeric member being made from an elastomeric material; and a means of engaging the proximal end of the inner elastomeric member to the proximal end of the cylindrical tube, wherein the means of engaging is an integral flange on the proximal end of the inner elastomeric member, the integral flange confines longitudinal movement of the proximal end of the inner elastomeric member when engaged with the proximal end of the cylindrical tube.

* * * * *